United States Patent [19]

Thüroff et al.

[11] Patent Number: 4,829,990
[45] Date of Patent: May 16, 1989

[54] IMPLANTABLE HYDRAULIC PENILE ERECTOR

[76] Inventors: Joachim Thüroff, Langenbeckstr. 1, 6500 Mainz, Fed. Rep. of Germany; German Borodulin, 2518 Clement St. #4, San Francisco, Calif. 94121; Alexander Shkolnik, 962 So. El Camino Real #202, San Mateo, Calif. 94402

[21] Appl. No.: 66,231

[22] Filed: Jun. 25, 1987

[51] Int. Cl.$^4$ .............................................. A61F 2/26
[52] U.S. Cl. ...................................... 128/79; 128/327
[58] Field of Search ................ 128/79, 327, DIG. 25, 128/1 R

[56] References Cited

U.S. PATENT DOCUMENTS

| | | | |
|---|---|---|---|
| 4,222,377 | 9/1980 | Burton | 128/DIG. 25 |
| 4,235,277 | 11/1980 | Yamanaka | 128/79 |
| 4,428,365 | 1/1984 | Hakky | 128/1 R |
| 4,592,339 | 6/1986 | Kuzmak et al. | 128/1 R |
| 4,632,114 | 12/1986 | Todd et al. | 128/DIG. 25 |

*Primary Examiner*—Gene Mancene
*Assistant Examiner*—Cary E. Stone
*Attorney, Agent, or Firm*—David Pressman

[57] ABSTRACT

An implantable hydraulic penile erectile device comprises a pair of occlusive cuffs (32 and 34) which are surgically implanted and wrapped around respective crura (18 and 20). The cuffs have expandable domes (56) on their inner surface (54). The domes are connected, via a check valve (44) and respective tubes (36, 38, 64, and 66), to a pump-reservoir (42). The pump-reservoir and the check valves are implanted in the scrotum. The system in general is filled with a working fluid so that when the pump-reservoir is squeezed, the working fluid is shifted to the expandable domes via the check valve. Expansion of the domes squeezes the crura of the penis and hence the deep penile veins (26a and 26b). This restricts venous blood flow from the cavernous bodies, causing engorgement of the spongy tissue and thus inducing erection. For deactivation of the device, the user squeezes the check valve so that bypass channels (68 and 70) are formed therein. Through these channels the fluid can return from the domes back to the pump-reservoir.

20 Claims, 2 Drawing Sheets

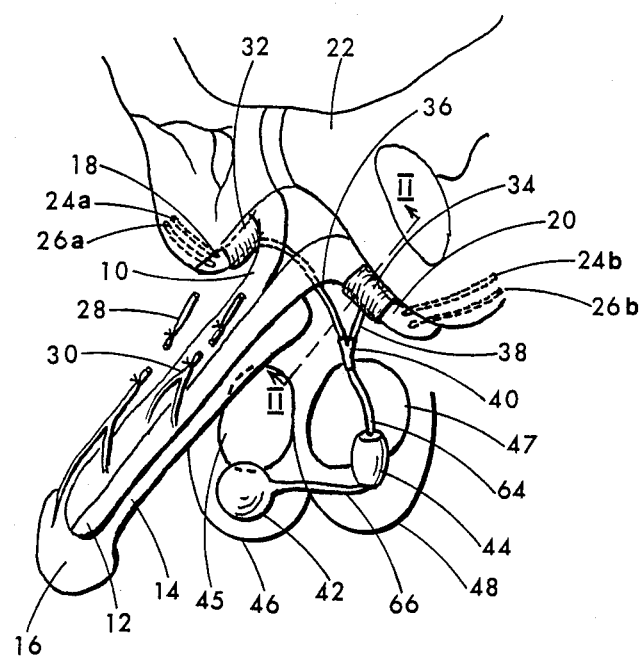
Fig. 1
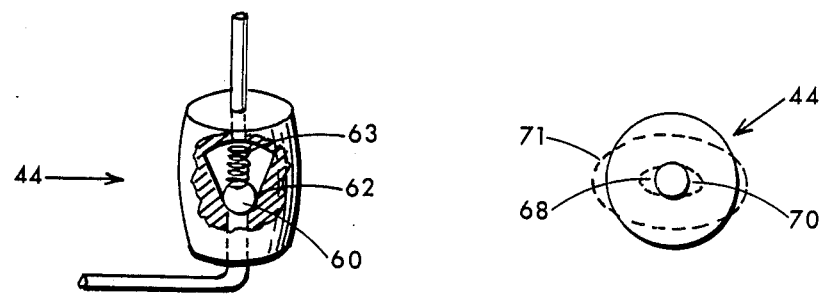
Fig. 5
Fig. 6

IMPLANTABLE HYDRAULIC PENILE ERECTOR

BACKGROUND—FIELD OF THE INVENTION

The present invention relates to a device implantable into a human body, particularly to an implantable device for creating penile tumescence where such function has been impaired.

BACKGROUND—DESCRIPTION OF THE PROBLEM

Penile erection (tumescence) is normally effected by increased arterial blood flow into the penis and by simultaneous restriction of the venous outflow. This hemodynamic (hydraulic blood) mechanism is governed by nervous impulses from the central and the peripheral autonomic nervous systems.

A man's failure to achieve penile erection usually is due to one or more of the following causes: neurologic diseases, psychological diseases, an impaired arterial blood supply, or a venous leak.

Herefore penile erectile disfunction was treated by medical therapy (oral drugs or direct penile injections), psychotherapy, surgical measures, and external appliances.

The surgical measures heretofore employed were revascularization (restoration of blood flow) in cases of impaired arterial inflow, correction and closure of venous leaks, or implantation of erectile devices.

The types of penile erectile devices (implantable and external) heretofore employed were as follows: 1) inflatable hydraulic cylindrical devices which were implanted relatively deeply into the cavernous bodies (corpus cavernosua—two elongated inflatable bodies running longitudinally at the top of the penis), exemplified in U.S. Pat. No. 4,424,807 to Evans, Sr., 1984; 2) semi-rigid or rigid rod-shaped devices which were implanted in the cavernous bodies, exemplified in U.S. Pat. No. 4,201,202 to Finney, 1980; 3) inflatable hydraulic subcutaneous (relatively shallow) implants, exemplified in U.S. Pat. No. 4,523,584 to Yachia, et al., 1985; and 4) external penile appliances, exemplified by U.S. Pat. No. 4,641,638 to Perry, 1987, and an implantable venous valve with external magnetic control, shown in U.S. Pat. No. 3,731,670 to Loe, 1973.

The disadvantage of implants in the cavernous bodies is that the surgery is destructive because some spongy tissue of the cavernous bodies must be removed. Also these implants do not restore the penis's physiological hemodynamic functions, but rather substitute an artificial mechanism, necessitating the aforementioned removal of anatomical penile structures.

The disadvantage of the semi-rigid and rigid rod-like implants is that they maintain the penis in a continuously erected state, which can be embarrassing, painful, and awkward for the patient. Subcutaneous implants result in encapsulation of the penis with possible loss of sensitivity. The implantable venous valve has not been tested and requires delicate surgery.

Surgical procedures which restore the natural physiological function of penile hemodynamics theoretically would be more desirable. These include procedures for arterial revascularization or repair of venous leaks. However, most of these surgical procedures have had a poor success rate, thereby limiting their practical application. Also many involve permanent percutaneous mechanisms; these create a risk of infection and are more susceptible to trauma.

OBJECTS AND ADVANTAGES OF THE PRESENT INVENTION

Therefore one object of the present invention is to provide an implantable hydraulic penile erector which can restore physiological erectile function without destroying or removing anatomical structures. Other objects are to provide a penile erector which can be used without the loss of sensitivity, which can be easily controlled at will of the user, which use the body's hemodynamic function, which do not create a continuous erection, and which do not require any permanent percutaneous mechanism. Other features and advantages of the invention will be understood after consideration of the ensuing description and the accompanying drawings.

DRAWINGS

FIG. 1 is a general perspective view of an implanted penile erector device according to the invention.

FIG. 5 is a schematic view of a check valve used in the implanted system.

FIG. 6 is a top view illustrating the check valve of FIG. 5 in its open or squeezed position.

Figure 2:
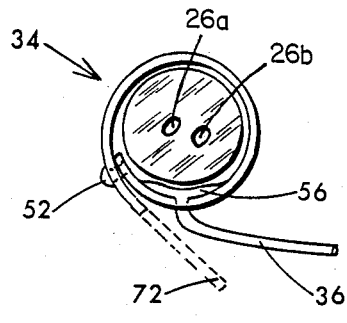
FIG. 2 is a sectional view showing an inflatable occlusive cuff in a deflated condition.

REFERENCE NUMERALS USED IN THE DRAWINGS 10, 12-cavernous bodies of the penis
14-spongy body of the urethra
16-glans penis
18, 20-crura penis
22-pelvic bone
24a, 24b-deep penile arteries
26a, 26b-deep penile veins
28-superficial dorsal vein
30-deep dorsal vein
32, 34-inflatable occlusive cuffs
36, 38-tubing of the occlusive cuffs
40-Y-shaped connector
42-pump-reservoir
44-check valve
45, 47
46, 48-scrotal pouches
50-holes in occlusive cuff
52-snap button
54-inner side of cuff
56-expandable dome
58-check valve body
60-ball in check valve
62-valve seat
63-spring
64, 66-tubes
68, 70-bypass channels
71-deformed valve body
72-excessive length of the cuff

FIG. 1—PENILE ANATOMY

For better understanding the principle of our invention, it is first necessary to describe some anatomical structures of the penis which are involved in the surgical technique associated therewith.

As shown in FIG. 1, which is a view taken from in front of the patient, to his left, the penile body is formed by two elongated cavernous bodies 10 and 12 and a spongy body 14. Spongy body 14 also forms glans 16 of the penis. The cavernous bodies have respective rear parts 18 and 20 which are attached to the public bone 22 and are called the crura (legs) of the penis. The blood supply to both cavernous bodies 10 and 12 is supplied by deep penile arteries 24a and 24b and is drained by veins 26a and 26b which leave the ends of crura 18 and 20. Additional venous drainage of cavernous bodies 10, 12, 14, and 16 is performed by a superficial dorsal vein 28 and a deep dorsal vein 30.

FIG. 1—PENILE ERECTOR

A general view of the penile erectile device of the invention, as implanted into the anatomical structures described above, is shown in FIG. 1.

The device comprises two inflatable occlusive cuffs 32 and 34; these are wrapped around respective crura 18 and 20. These cuffs are connected via tubes 36 and 38 to a Y-shaped joint or connector 40, which in turn is connected to a pump reservoir 42 through a check valve 44. Connector 40 is a standard part for implantable hydraulic devices and may be made of metal or plastic.

Pump reservoir 42 is implanted in one scrotal pouch 46, while check valve 44 is implanted into the contralateral (other) scrotal pouch 48. For exemplary purposes, reservoir 42 is implanted in the right pouch and valve 44 in the left, although this arrangement can be reversed. The implanted parts, i.e., check valve 44 and pump reservoir 42 are located subcutaneously outside the sleeve of testicles, and therefore do not interfere with them. In practice parts 42 and 44 lie below the testicles (not shown).

FIGS. 2 TO 6—CONSTRUCTION OF OCCLUSIVE CUFFS, VALVE AND OTHER ELEMENTS OF THE PENILE ERECTOR

Now the separate elements of the penile erector of the invention will be described in detail with reference to FIGS. 2 to 6.

Figure 3:
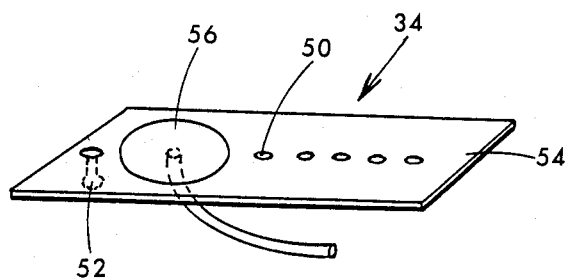
FIG. 3 is a perspective view of the occlusive cuff in its open condition prior to implantation.

FIG. 2 shows one of the occlusive cuffs (34) in cross section. As both occlusive cuffs are identical, only one of them (34) will be described. In its working or implanted state, cuffs 32 and 34 are wrapped around respective crura 18 and 20, with cuff 34 shown around crus 20. Cuff 34 is locked in the wrapped position as shown by means of a locking device. As is shown in FIG. 3, a view of the occlusive cuff in the open position, this locking device comprises a series of holes 50 formed adjacent one end of the cuff and a snap button 52 which is at the other end of the cuff. Button 52 can mate with any one of holes 50 so that the circumferential length of the cuff to be adjusted so that it can fit snugly around its crus.

On its inner side 54, which faces crus 20, each cuff has an inflatable dome or bladder 56. Dome 56 of cuff 34 is connected to tube 38, the tube being attached to the dome through the wall of the cuff. Cuff 32 and its elements have the same construction and arrangement as cuff 34.

Each of the cuffs is made of a non-expandable material, preferably the cloth sold under the trademark DACRON and coated with silicone. The only expandable part of the cuff is dome 56 which is made of silicon without reinforcement. A typical cuff may be 2 cm wide, 7.5 cm long and 1 mm thick. Dome 56 may occupy the entire width of the cuff and have a thickness of about 0.1 mm. When inflated, dome will rise from 0.1 mm to about 1 cm high, as measured from inner surface 54 of the cuff. The connecting tubes between the elements of the device, i.e., tubes 36, 38, 64, and 66, are made of silicone and have an outside diameter of about 3 mm and an inner diameter of about 1.5 mm.

Figure 4:
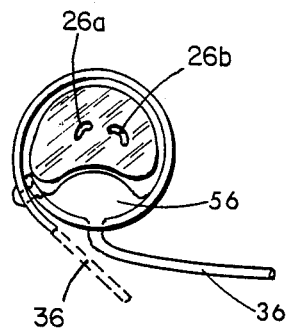
FIG. 4 is a view similar to that of FIG. 2 with the occlusive cuff in its inflated condition.

FIG. 4 illustrates cuff 34 with dome 56 in its inflated state. As shown, when dome 56 is implanted, it compresses crus 20 and hence deep penile vein 26b. This action and its results will be described in detail later with reference to operation of the device.

A schematic view of check valve 44 is shown in FIG. 5. The valve comprises a valve body 58 made of a resilient material such as silicone. Located inside valve body 58 is a ball element or obturator 60 which is constantly pressed to a valve seat 62 by a spring 63. Valve 44 is connected to Y-type connector 38 by a tube 64, while the part of the valve on the opposite side of ball 62 is connected via tube 66 to pump reservoir 42. Valve 44, pump-reservoir 42 and tube 66 preferably are molded together as an integral unit.

As is shown in FIG. 1, pump reservoir 42 is made in the form of a resilient spherical body which fulfills two functions, i.e., it works as a pump and at the same time as a container for the working fluid (not shown). A working fluid suitable for the purpose of the present invention may comprise an isotonic solution, such as normal saline water, or a solution of contrast dye in distilled water.

Check valve body 58 has a cylindrical shape with an outer diameter of about 1.5 cm and a height of 2 cm. Ball 60 of the check valve may have a diameter of about 4 mm. The dimensions of pump-reservoir 42 should be such that it can hold a volume of approximately 10 cubic cm, but in general the diameter of pump-reservoir 42 should not exceed 3 cm.

FIG. 6 shows check valve 44 in its open condition; this is created by squeezing valve body 58. In the inflated state of the domes, ball 60 is pressed to its seat 62 by force of spring 63 assisted by pressure of the working fluid in the system. Thus the valve is closed. When the valve is squeezed, ball 60 is shifted up from its seat, forming bypass channels 68 and 70 for fluid on both side of ball 60. These allow the fluid to return into pump reservoir 42 under its own pressure.

FIGS. 1 TO 3—SURGICAL IMPLANTATION

Prior to implantation, all parts of the device are filled with the working fluid so that the completed system will be free of air. To implant the erector device, a skin incision is made on the dorsal side of the penis to expose the crura at the site of intended implantation.

For implantation of inflatable occlusive cuffs 32 and 34, crura 18 and 20 of the penis are separated from pelvic bone 22 for over a length of approximately 2.5 cm at locations adjacent and distal to the point of entry of deep penile arteries 24a, 24b and veins 26a, 26b. This creates a space between the crus and the pubic bone. Because the arrangement of both crura is symmetrical and identical, all further operations will be described with reference to one of the cuffs, for example, cuff 34 associated with crus 20.

The end of cuff 34 opposite to dome 56 is pulled through the space created between crus 20 and pubic bone 22. The orientation of cuff 34 has to be such that inner side 54 of the cuff and expandable dome 56 face crus 20. The end of cuff 34 is then wrapped around crus 20 and closed by inserting button 52 onto one of holes 50. As shown in FIG. 2, closed cuff 34 should fit the size of respective crus 20 snugly, but without constricting it. Any excessive lenght 72 of cuff 34, which is shown by broken lines in FIG. 2, is then cut off and discarded. As has been mentioned before, cuff 32 is implanted in the same manner.

The next step of the procedure is implantation of pump-reservoir 42 and check valve 44. An incision is made on each side of the scrotum, and subcutaneous spaces are created in both scrotal pouches. Pump-reservoir 42 is inserted in one side 46 of the scrotum, while check valve 44 is placed in the contralateral scrotum side 48.

Both tubes 36 and 38, which come from occlusive cuffs 32 and 34, respectively, and tube 64, which comes from check valve 44, are trimmed to an appropriate length for connection to the legs of Y-shape connector 40. To ensure reliable connection and sealing, the connections between tubes 36, 38, and 64 and the legs of Y-shape connector 40 are reinforced by sutures (not shown).

At this stage, the penile erectile prosthetic device of the invention is completely implanted, assembled, and fluid-filled. To complete the operation, superficial dorsal vein 28 of the penis and deep dorsal vein 30 are cut and their cut ends are tied (as indicated) to interrupt venous drainage of the cavernous bodies through these veins, so that cuffs will be able to cut off virtually all vena's drainage from the cavernous bodies. Following this, the separated body tissues are reapproximated by sutures, and the incisions are closed.

FIGS. 1, 4 AND 6—OPERATION

After healing, the patient can achieve erection easily. Prior to intercourse, he palpates (feels) and compresses pump-reservoir 42 through the scrotal skin. This will force a portion of the working fluid (not shown) from pump-reservoir 42 through tube 66 to check valve 44. Fluid pressure will overcome the force of spring 63 and raise ball 60 from its seat 62, allowing the fluid to flow through gaps between ball 60 and seat 62 to tube 64. The fluid then passes through Y-shaped connector 40 and tubes 36 and 38 into inflatable domes 56 of both occlusive cuffs 32 and 34. The fluid thereupon inflates domes 56 within cuffs 32 and 34, as shown in FIG. 4. This will squeeze crura 18 and 20 of the penis and hence compress deep penile veins 26a and 26b, as indicated. As superficial dorsal vein 28 and deep dorsal vein 30 have been closed as part of the surgical procedure, the only remaining place for venous drainage will be through deep penile veins 26a and 26b. Since the latter have been compressed, this will restrict (but not completely block to prevent gangrene) outflow of blood from cavernous bodies 10 and 12, thus inducing their engorgement. This is the natural physiological mechanism of erection.

To disactivate the device after intercourse, the user need merely squeeze his scrotum at the appropriate place to compress check valve 44. This will deform body 58 from its normal cylindrical shape (shown by the solid line in FIG. 6) to the oval shape, shown by broken line 71. The result is the formation of by-pass channels 68 and 70 within check valve 44. These channels allow a back flow of the working liquid under inner pressure of the system from domes 56 through tubes 36, 38 64, and 66 to pump-reservoir 42. Being released from pressure, domes 56 will deflate, releasing the pressure on crura 18 and 20 and deep penile veins 26a and 26b; vein 26b is indicated in FIG. 2. Thereupon venous blood flow from cavernous bodies 10 and 12 will return and the erection will be reversed.

CONCLUSION, RAMIFICATIONS AND SCOPE

Thus it has been shown that the implantable device of the invention provides a hydraulic penile erector which can restore physiological erectile function by restricting venous outflow without removing spongy tissue of the cavernous bodies of the penis, and without loss of sensitivity. The device uses the body's hemodynamic functions, do not crate a continuous erection, and do not require any permanent percutaneous mechanism. The device can be easily controlled at will of the user.

Although the device has been described with reference to a specific embodiments of its parts and elements, it should be understood by those skilled in the art that the structural features and dimensions mentioned in the description were given for illustrative purposes only and should not be construed as limiting the scope of the invention. For example, other biocompatible resilient materials than silicone can be used for the manufacture of components of the device. Valve body 58 may have a spherical or cubical shape instead of cylindrical and may be released by other means. Other expandable means such as cylinder-piston units may be used instead of the inflatable domes. In lieu of a belt with an inflatable dome, the apparatus may employ a double-layered belt with an inflatable internal chamber (similar to that used in blood pressure apparatus cuffs) with multiple hook-and-loop fastener end attachments. Placement of pump-reservoir 42 and check valve 44 in the right and left scrotal pouches respectively is most suitable for a right-handed person. It is understood, therefore, that these positions may be reversed for a left-handed person is also within the scope of the invention. The pump mechanism may be combined with the check valve as one unit. Also the pump-reservoir and check valve may be implanted elsewhere than the scrotal pouches, e.g., in the lower abdomen, adjacent the pubic bone. Thus the scope of the invention should be determined not by examples given, but rather by the appended claims and their legal equivalents.

We claim:

1. An implantable hydraulic penile erectile device, comprising:
   a pair of compression means engageable with the crura of the penis for compressing said crura and the deep penile veins therein when activated and for releasing said crura and said deep penile veins when deactivated;
   each of said compression means being implanted into the penis and extending around a respective crus, and
   control means for selectively activating or deactivating said compression means,
   whereby said control means can be used selectively to cause said penis to become flaccid or erect.

2. The erectile device of claim 1 wherein said control means comprises a pump-reservoir and a valve.

3. The implantable penile erector of claim 2 wherein said pump reservoir comprises a container made of a resilient material and filled with a working fluid.

4. The implantable penile erectile device of claim 2 wherein said valve comprises a check valve.

5. The implantable penile erectile device of claim 2 wherein each of said compression means comprises an inflatable belt made of a flexible non-stretchable material with an inflatable bladder on a part of its inner surface, said belt extending around the respective crura of the penis, and including tubing connecting said valve and said pump-reservoir to the interior of said bladder.

6. The inflatable penile erectile device of claim 5 wherein each of said inflatable belts includes locking means for fixing said belt around its respective crus, said locking means comprising a snap button on the outer surface of one end of said belt and a series of mating sequential holes in said belt at the other end thereof.

7. The inflatable penile erectile device of claim 5 wherein said non-stretchable flexible material comprises reinforced silicone and said inflatable means comprises a dome-like bladder made of a film-like silicone.

8. The inflatable penile erectile device of claim 2 wherein said pump-reservoir and said valve are made of a flexible material.

9. The inflatable penile erectile device of claim 8 wherein said flexible material is made of a biocompatable silicone.

10. An implantable hydraulic penile device comprising:
   a pump-reservoir which is filled with a working fluid;
   a releasable check valve connected to said pump-reservoir by a first flexible tube;
   a pair of compression means engageable with the respective crura of the penis and connected by second and third flexible tubes to said check valve, said compression means each being arranged to compress a respective crus and the deep penile vein therein when activated and to release said crus and said deep penile vein therein when deactivated;
   each of said compression means being implanted into the penis and extending around its respective crus, whereby said control means can be used selectively to cause said penis to become flaccid or erect.

11. The implantable penile erectile device of claim 10 wherein each of said compression means comprises an inflatable belt made of a flexible non-stretchable material with an inflatable means on a part of its inner surface, each of said belts being wrapped around a respective crus of the penis and having means for locking it in its wrapped position, said second and third flexible tubes being connected to the interior of said inflatable belts for supplying fluid to said inflatable means from said pump-reservoir through said check valve.

12. The inflatable penile erectile device of claim 11 wherein said means for locking comprises a snap button on the outer surface of said belt and on one end thereof, and a plurality of sequential holes formed in said belt on the other end thereof, said button being engageable with said holes for locking said compression means in their wrapped position.

13. The inflatable penile erectile device of claim 11 wherein said non-stretchable flexible material comprises reinforced silicone and said inflatable means comprises a dome-like element made of a film-like silicone.

14. The inflatable penile erectile device of claim 13 wherein said silicone is biocompatable.

15. The implantable hydraulic penile erectile device of claim 10 wherein said pump-reservoir is implanted in the scrotum.

16. A method for selectively creating a penile erection, comprising:
   providing means, which, when activated, will compress both crura of the penis and hence the deep penile veins therein sufficiently to cause said penis to become erect, and when deactivated, will allow said penis to become flaccid;
   providing control means for selectively activating or deactivating said compression means; and
   causing said control means to activate said compression means when an erection is desired and deactivate said compression means when an erection no longer is desired.

17. The method of claim 16 wherein said control means comprises a pump-reservoir and a valve and said control means is operated by compressing said pump-reservoir and opening said valve.

18. The method of claim 16, further including the step of implanting said control means in the scrotum.

19. The method of claim 16 wherein said compression means comprises a pair of inflatable belts, each made of a flexible non-stretchable material with an inflatable means on a part of its inner surface, each of said belts being wrapped around a respective crus of the penis and having means for locking it in its wrapped position, and said control means is operated to cause said belts to become inflated or deflated.

20. The method of claim 19 wherein said non-stretchable flexible material comprises reinforced silicone and said inflatable means comprises a dome-like element made of a film-like silicone, and further including the step of surgically implanting said belts in the penis and around their respective crura.

* * * * *